(12) United States Patent  
Paul (10) Patent No.: US 6,503,250 B2
(45) Date of Patent: Jan. 7, 2003

(54) BONE SUPPORT ASSEMBLY (76) Inventor: Kamaljit S. Paul, 3220 Old Orchard La., Oshkosh, WI (US) 54901

( * ) Notice: Subject to any disclaimer, the term of this patent is extended or adjusted under 35 U.S.C. 154(b) by 0 days.

(21) Appl. No.: 09/838,646

(22) Filed: Apr. 19, 2001

(65) Prior Publication Data

US 2002/0065517 A1 May 30, 2002

Related U.S. Application Data (60) Provisional application No. 60/253,437, filed on Nov. 28, 2000.

(51) Int. Cl.[7] .............................................. A61B 17/80
(52) U.S. Cl. ...................................................... 606/69
(58) Field of Search ............................. 606/60, 61, 69, 606/70, 71

(56) References Cited

U.S. PATENT DOCUMENTS

| | | | |
|---|---|---|---|
| 4,503,848 A | | 3/1985 | Caspar et al. |
| 5,324,290 A | | 6/1994 | Zdeblick et al. |
| 5,344,421 A | | 9/1994 | Crook |
| 5,616,144 A | * | 4/1997 | Yapp et al. ................... 606/61 |
| 5,676,666 A | | 10/1997 | Oxland et al. |
| 5,681,311 A | | 10/1997 | Foley et al. |
| 5,728,127 A | | 3/1998 | Asher et al. |
| 5,904,683 A | | 5/1999 | Pohndorf et al. |
| 5,951,558 A | * | 9/1999 | Fiz .............................. 606/70 |
| 5,954,722 A | | 9/1999 | Bono |
| 6,017,345 A | | 1/2000 | Richelsoph |
| 6,030,389 A | | 2/2000 | Wagner et al. |
| 6,106,557 A | | 8/2000 | Robioneck et al. |
| 6,129,730 A | | 10/2000 | Bono et al. |
| 6,139,550 A | * | 10/2000 | Michelson ................... 606/69 |
| 6,152,927 A | * | 11/2000 | Farris et al. .................. 606/69 |
| 6,159,213 A | | 12/2000 | Rogozinski |
| 6,224,602 B1 | * | 5/2001 | Hayes ........................ 606/69 |
| 6,235,034 B1 | * | 5/2001 | Bray ............................ 606/71 |
| 6,293,949 B1 | * | 9/2001 | Justis et al. ................... 606/61 |
| 6,306,139 B1 | * | 10/2001 | Fuentes ......................... 606/70 |

FOREIGN PATENT DOCUMENTS

| | | |
|---|---|---|
| WO | WO 00/24325 | 5/2000 |
| WO | WO 00/64359 | 11/2000 |
| WO | WO 01/26566 | 4/2001 |

OTHER PUBLICATIONS

Health Journal, Tara Parker–Pope, The Wall Street Journal, Jan. 2001, 1 sheet.

C–TEK Anterior Cervical Plate, 2001 Interpore Cross International, 1 sheet.

C–TEK Anterior Cervical Plate system, Interpore Cross, Oct. 2000, 1 sheet.

WINDOW Cervical Stabilization System, 2000 Endius, Inc., 10 sheets.

(List continued on next page.)

Primary Examiner—Eduardo C. Robert
(74) Attorney, Agent, or Firm—Wilhelm Law Service; Thomas D. Wilhelm (57) ABSTRACT

A bone support assembly comprising a support plate, bone fasteners, and a bone fastener cover assembly. The support plate comprises a fixed base portion comprising base apertures, and a slot portion comprising slot-shaped apertures. The bone fasteners are disposed in ones of the base apertures and the slot-shaped apertures, the bone fasteners and the support plate, in combination, being adapted and configured for holding the support plate to bone material. The bone fastener cover assembly comprises a cover plate, and at least one cover plate fastener effective to fasten the cover plate to the support plate. The cover plate and support plate, in combination, accommodate both longitudinal and transverse sliding movement of the cover plate along the top surface of the support plate to thereby cover and uncover ones of the apertures, having bone fasteners therein, while the cover plate is attached to the support plate.

40 Claims, 5 Drawing Sheets

OTHER PUBLICATIONS

CASPAR Instruments for Anterior Cervical Fusion, AESCULAP, undated. 4 sheets.

NDC Internet Data Sheets, date unknown, 3 sheets.

Ni–Ti alloy Internet Data Sheets, date unknown, 4 sheets.

"Blackstone™ Anterior Cervical Plate." Blackstone Medical Inc. Product literature. 4 sheets. No date available.

"CSLP Variable Angle: For Use with the Cervical Spine Locking Plate System." Technique Guide. 2000 SYNTHES® Spine. 28 sheets.

Zdeblick, M.D., Thomas A. et al. "Premier™ Anterior Cervical Plate System." Surgical Technique. 2000 Medtronic Sofamor Danek. 30 sheets.

* cited by examiner

BONE SUPPORT ASSEMBLY

BACKGROUND

The present invention relates to devices for the fixation and/or support of bones. In particular, the present invention relates to a plate for the fixation and/or support of bones of the spinal column. The plate of the present invention has particular application in situations where compressional or "settling" forces, as well as torsional and flexing forces, of "fixed" vertebrae on a spinal plate cause significant stressing and potential failure of the spinal plate and/or plate components.

Vertebral fixation has become a common approach to treating spinal disorders, fractures, and for fusion of vertebrae at the time such fixation is instituted. Namely, one or more vertebrae are fixed in position relative to one or more other vertebrae above and/or below the vertebrae to be fixed. Generally, a spinal plate is the device of choice used for mechanically supporting such vertebral fixation. A typical spinal plate includes a plate having a plurality of apertures therethrough. A corresponding plurality of fasteners, i.e., bone screws, are generally positioned into and through respective apertures of the plate to secure the spinal plate to a bone, such as two respective upper and lower supporting adjacent spinal vertebrae. The screws are fastened to the respective support vertebrae to secure the spinal plate to the respective vertebrae. In general, such plate and screw assemblies can be utilized, generally, for anterior fixation of the spine for cervical, lumbar, and/or thoracic fixation.

The basis of anterior fixation or plating is to approach the spine from an anterior or anterio-lateral approach, and use the screws to solidly mount the spinal plate to the affected vertebrae. Often, in addition to the application of a spinal plate, graft material may be combined in attempt to permanently fuse together adjacent vertebrae. The graft material can consist of bone grafts obtained from bones of the recipient or another individual.

A common problem associated with the use of such spinal plates is the tendency of the bone screws to "back out" or pull away from the bone into which they are fixed. This problem occurs, primarily, due to the normal torsional and bending motions of the body and spine. This is a particularly important problem because as the screws become loose and pull away from the bone, the heads of the screws can rise above the surface of the spinal plate and, possibly, even work their way completely out of the bone. While this condition can cause extreme discomfort for the recipient, this condition can also create a number of potentially serious physiological problems given the significant amount of nervous and vascular structures associated at or near the potential locations of anterior spinal plate fixations.

A number of designs have been proposed in attempts to prevent screws from pulling away from the bone and/or to prevent the screws from backing out or pulling away from the surface of the spinal plate. Such mechanisms used to prevent bone screws from pulling out of bones include cams which engage and lock the screws, and the use of expanding head screws which expand outwardly when adequate force is applied thereto to engage the holes in the spinal plate. All of these designs have detriments including potential for breakage or requiring particular precision and alignment in their application in order to work correctly. Additionally, loose components and accessories of spinal plates which address the "backing-out" problem can get dropped and/or misplaced while the vertebral fixation surgical procedure is taking place, prolonging and complicating the procedure as well as creating substantial risk of harm to the recipient.

Yet another common problem associated with the use of such spinal plates is the tendency of the vertebrae being "fixed" to settle after spinal plate insertion adding compression forces to the above-listed forces which cause the bone screws to "back out" or pull away from the bone into which they were fixed. Zdeblick et al. (U.S. Pat. No. 5,324,290) attempted to address the problem of compression forces in the context of treating vertebral burst fractures, but fails to provide any functional means to prevent the screws pulling away as a result of torsional and flexing forces.

Therefore, it is an object of the invention to provide bone fixation apparatus which provides rigid bone-to-bone fixation and/or support, such as e.g. adjacent or second adjacent vertebrae, while allowing post-procedural compression between the respective bones.

It is another object of the invention to provide bone fixation apparatus which affords substantial protection against pulling away of affixing components which may result from torsional movement, flexing movement, or stress and/or dynamic load sharing of the vertebrae, thereby enhancing the bone rebuilding process.

It is yet another object of the invention to provide bone fixation apparatus which attenuates application of stress on the apparatus and affixing components. It is a further object of the invention to provide bone fixation apparatus comprising a support plate and fixation components, and fixation component support which reinforces the fixation components thus to prevent the fixation components from backing out of the support plate.

It is yet a further object of the invention to provide bone fixation apparatus which can be pre-assembled as a loose assembly such that no loose assembly parts or inter-procedural apparatus need be assembled to the assembly during installation of such bone fixation apparatus in a recipient.

SUMMARY

In a first family of embodiments, the invention comprehends a bone support plate for use in a bone support assembly. The bone support plate comprises a top surface, a bottom surface opposite the top surface and adapted to engage bone structure of a user; a fixed base portion, having first and second apertures extending therethrough, from the top surface to the bottom surface, for receiving bone fasteners therethrough, and a slot portion, having at least third and fourth apertures extending therethrough, from the top surface to the bottom surface, for receiving bone fasteners therethrough. A first base cover plate recess is disposed in the top surface at the fixed base portion for receiving a base cover plate thereonto and accommodating sliding movement of such base cover plate to impose and withdraw at least partial obstruction of the first and second apertures. Similarly, a second settle cover plate recess is disposed in the top surface at the slot portion for receiving a settle cover plate thereonto and accommodating sliding movement of such settle cover plate to impose and withdraw at least partial obstruction of the third and fourth apertures.

In preferred embodiments, the bone support plate is designed and configured to enable bidirectional sliding movement of a base cover plate connected thereto, wherein the bidirectional sliding movement is in substantial alignment with the top surface of the bone support plate.

Preferably, the bone support plate is designed and configured to enable bidirectional sliding movement of a settle cover plate connected thereto, wherein the bidirectional sliding movement is in substantial alignment with the top surface of the bone support plate.

In some embodiments, the bone support plate comprises a base cover plate fastener aperture extending therethrough, from the first base cover plate recess to the bottom surface of the bone support plate, for receiving a base cover plate fastener therethrough.

In some embodiments, the bone support plate comprises a settle cover plate fastener aperture extending therethrough, from the second settle cover plate recess to the bottom surface of the bone support plate, for receiving a settle cover plate fastener therethrough.

In some embodiments, at least a portion of the bottom surface of the support plate comprises a texturized surface, the texturized surface enhancing engagement of the support plate to the bone structure.

The apertures of the slot portion are preferably longitudinally slot-shaped, with respect to a longitudinal axis of the support plate, to enable respective bone fasteners to be inserted into the respective apertures such that the slot-shaped apertures accommodate movement of the bone support plate with respect to the bone fasteners.

In preferred embodiments, the support plate is curved to conform the support plate to the curvature of corresponding vertebrae.

In a second family of embodiments, the invention comprehends a bone support assembly comprising a support plate, bone fasteners, and a bone fastener cover assembly. The support plate comprises a top surface, a bottom surface adapted to engage such bone structure, a fixed base portion comprising base apertures, and a slot portion comprising slot-shaped apertures. The bone fasteners are disposed in ones of the base apertures and the slot-shaped apertures, the bone fasteners and the support plate, in combination, being adapted and configured for holding the support plate to bone material. The bone fastener cover assembly comprises a cover plate, and at least one cover plate fastener effective to fasten the cover plate to the support plate. The at least one cover plate and the support plate, in combination, accommodate both longitudinal and transverse sliding movement of the cover plate along the top surface of the support plate, with respect to a longitudinal axis of the support plate, to thereby cover and uncover ones of the bone fasteners while the cover plate is attached to the support plate, including uncovering one of a pair of bone fasteners arranged in side-by-side relationship along the longitudinal axis of the support plate, while relatively covering the other of such pair of bone fasteners.

In some embodiments, at least a portion of the bottom surface of the support plate comprises a texturized surface, the texturized surface enhancing engagement of the support plate to bone material.

In preferred embodiments, the slot-shaped apertures are designed and configured to receive respective ones of the bone fasteners into respective slot-shaped apertures such that ones of the bone fasteners can move about freely within the apertures.

Preferably, the cover plate of the bone fastener cover assembly simultaneously covers, at least in part, bone fasteners in at least 4 slot-shaped apertures of the support plate, where one or both longitudinal and transverse movement of the cover plate tends to simultaneously cover a bone fastener in at least one aperture while uncovering another bone fastener in another aperture, whereby at no time are the bone fasteners in all apertures uncovered.

In a third family of embodiments, the bone support assembly comprises a support plate, bone fasteners, a base portion cover assembly disposed at the fixed base portion, and a slot portion cover assembly disposed at the slot portion.

In preferred embodiments, the base portion cover assembly comprises a base cover plate having an upper surface and a lower surface, at least one base cover plate fastener, and at least one base cover plate aperture spanning from the upper surface of the base cover plate to the lower surface of the base cover plate.

Preferably, the size of the at least one base cover plate aperture is greater than a corresponding size of at least one base cover plate fastener by a first dimension greater than or substantially equal to that amount of bidirectional movement of the base cover plate about the base cover plate fastener relative to the support plate necessary to gain fastening access to at least one bone fastener of the support plate while prohibiting fastening access to at least another bone fastener, whereby at no time are all bone fasteners accessible for fastening to the bone structure.

In some embodiments, the at least one base cover plate aperture comprises an aperture wall, wherein an upper portion of the aperture wall comprises an inwardly-tapered frustoconical configuration extending inwardly toward the lower surface of the base cover plate.

In preferred embodiments, the connection of the base portion cover assembly to the support plate is achieved by inserting the base cover plate fastener through the base cover plate aperture of the base cover plate and into a first base cover plate fastener aperture in the support plate, at least a portion of a wall of the first base cover plate fastener aperture being designed and configured to create a locking engagement relationship with the base cover plate fastener, the locking engagement relationship effectively preventing autonomous backing out of the base cover plate fastener from the first base cover plate fastener aperture.

In some embodiments, the locking engagement relationship is formed by the base cover plate fastener, having threading of a first wider pitch, being engaged against the wall of the first base cover plate fastener aperture, having threading of a second narrower pitch, whereby communication between the first and second threadings prevents autonomous backing out of the base cover plate fastener.

In other embodiments, the locking engagement relationship is formed by the base cover plate fastener, having threading, being engaged against the wall of the first base cover plate fastener aperture, comprising a shim or lock-ring having cooperative threading to that of at least a portion of the base cover plate fastener, whereby communication between the base cover plate fastener and the shim or lock-ring of the wall of the first base cover plate fastener aperture prevents autonomous backing out of the base cover plate fastener.

Preferably, the base cover plate overlaps a portion of at least one bone fastener in at least one of the base apertures of the support plate.

In preferred embodiments, the bone support assembly includes a slot in at least one of the base cover plate and the support plate, accommodating sliding of the base cover plate into overlying relationship with first ones of the bone fasteners, and out of overlying relationship with second ones of the bone fasteners.

In preferred embodiments, the base cover plate and the support plate, in combination, are designed and configured to enable bidirectional adjustment of the base cover plate, with respect to the support plate, while maintaining the support plate connected to the base cover plate.

The slot portion cover assembly preferably comprises a settle cover plate having a superior surface and an inferior surface, at least one settle cover plate fastener, and at least one settle cover plate aperture spanning from the superior surface to the inferior surface of the settle cover plate.

In some embodiments, the at least one settle cover plate aperture comprises an aperture wall, wherein an upper portion of the aperture wall comprises an inwardly-tapered frustoconical configuration adjacent the superior surface of the settle cover plate and extending toward the inferior surface of the settle cover plate.

In preferred embodiments, the connection of the slot portion cover assembly to the support plate is achieved by inserting the settle cover plate fastener through the settle cover plate aperture of the settle cover plate, from the superior surface to the inferior surface, and into a second settle cover plate fastener aperture in the support plate, at least a portion of a wall of the second settle cover plate fastener aperture being designed and configured to create a locking engagement relationship with the settle cover plate fastener, the locking engagement relationship effectively preventing autonomous backing out of the settle cover plate fastener from the second settle cover plate fastener aperture.

In some embodiment, the locking engagement relationship is formed by the settle cover plate fastener, having threading of a first pitch, being engaged into the second settle cover plate fastener aperture, having threading of a second pitch, whereby friction between first and second threadings prevents autonomous backing out of the settle cover plate fastener.

In other embodiments, the locking engagement relationship is formed between the settle cover plate fastener and a shim in the second settle cover plate fastener aperture, wherein the shim has cooperative threading to that of the settle cover plate fastener, whereby tension forces between the settle cover plate fastener and the shim of the second settle cover plate fastener aperture prevents autonomous backing out of the settle cover plate fastener.

The settle cover plate preferably overlaps a portion of at least one bone fastener in at least one slot-shaped aperture of the support plate.

In preferred embodiments, the settle cover plate and the support plate are, in combination, designed and configured to enable bidirectional adjustment of the settle cover plate, with respect to the support plate, while maintaining the support plate connected to the base cover plate.

In a fourth family of embodiments, the invention comprehends a method of mounting a support to bone structure. The method comprises providing a herein-described bone support assembly, moving the bone support assembly into position over bone structure to be supported, sliding the base cover plate away from the base apertures and fastening the bone fasteners, disposed in the base apertures, to the bone structure, and sliding the base cover plate at least partially over the bone fasteners disposed in the base apertures and tightening the base cover plate to the support plate thereby to prevent movement of the base cover plate and correspondingly preventing extraction of the bone fasteners in the base apertures.

In preferred embodiments, the method further includes sliding the settle cover plate away from respective ones of the bone fasteners disposed in the slot-shaped apertures and fastening the respective bone fasteners, in the slot-shaped apertures, to the bone structure. In such preferred embodiments, the method also includes sliding the settle cover plate at least partially over the respective fastened bone fasteners and tightening the settle cover plate to the support plate thereby to prevent movement of the settle cover plate, and correspondingly preventing extraction of the fastened bone fasteners.

The invention is not limited in its application to the details of construction or the arrangement of the components set forth in the following description or illustrated in the drawings. The invention is capable of other embodiments of being practiced or carried out in other various ways. Also, it is to be understood that the terminology and phraseology employed herein is for purpose of description and illustration and should not be regarded as limiting. Like reference numerals are used to indicate like components.

DESCRIPTION OF THE ILLUSTRATED EMBODIMENTS

Figure 1:
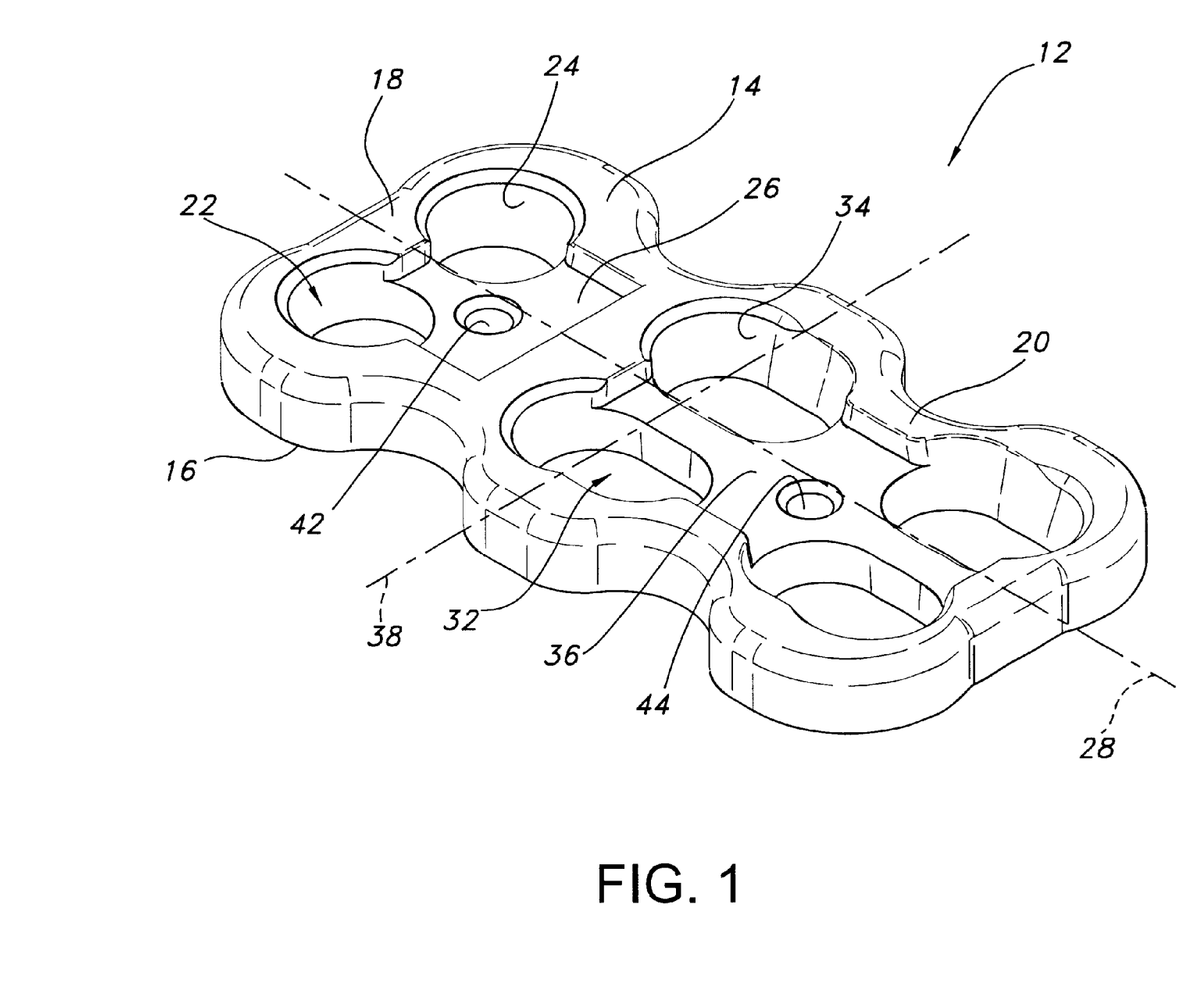
FIG. 1 is a pictorial view of a bone support plate of the invention.

Referring to FIG. 1, bone support assembly 10 (FIGS. 2–4) of the invention includes a substantially flat elongate support plate 12. Support plate 12 comprises a fixed base portion 18 and a slot portion 20. The elongate support plate 12 also includes a top surface 14 and a bottom surface 16, the bottom surface generally being adapted to engage the vertebrae. The length "L" of the elongate support plate, along one or both bottom surface 14 and top surface 16, from a most remote portion of fixed base portion 18 to a most remote portion of slot portion 20 should be sufficient enough to span between desired vertebrae. Support plate 12 also has a width "W". While support plate 12 is illustrated in FIGS. 1–5B as being substantially flat, other embodiments are contemplated wherein the support plate is arcuately shaped or curved along one or both longitudinal axis 28 and transverse axis 38 to conform the support plate to the curvature of the vertebrae to which such support plate will be affixed. Utilization of a curved or formed support plate can be incorporated into any embodiment of the bone fixation assembly in accordance with the present invention and is not limited by the specific embodiments disclosed herein, which are provided as examples of the possible designs which can be utilized with the present invention.

Base apertures 22, comprising aperture walls 24, are disposed in fixed base portion 18 of support plate 12. Similarly, slot-shaped apertures 32, comprising aperture walls 34, are disposed in slot portion 20 of support plate 12. Apertures 22, 32 are generally designed and configured to enable a respective shaft of a respective bone fastener to pass through a respective aperture to provide a fixation means of attaching support plate 12 of the bone support assembly to respective support vertebrae. The placement of the additional apertures in support plate 12 is contemplated, and depends upon the application to which the bone support assembly is to be applied.

Figure 5A:
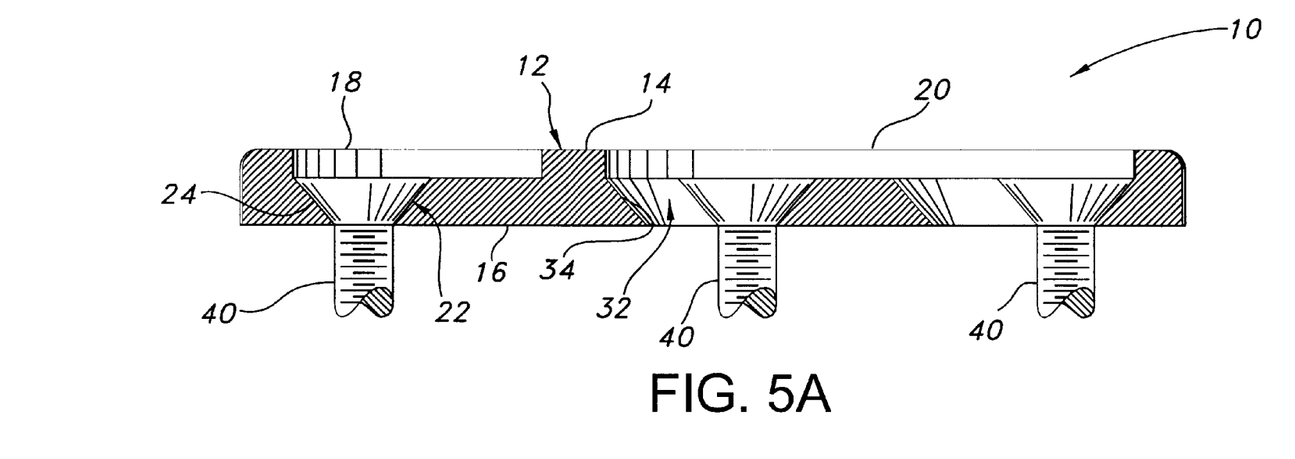
FIGS. 5A and 5B show cross-sectional views of two embodiments of the invention illustrating relationships between respective bone fasteners and apertures of the respective support plate.

Numerous embodiments of the invention are contemplated. Referring to FIG. 5A, ones of apertures 22, 32 are preferably designed and configured to demonstrate a frustoconical shape wherein at least parts of walls 24, 34 of respective apertures 22, 32 are tapered inwardly so as to reflect a relatively smaller cross-sectional opening at or near bottom surface 16, and correspondingly, a relatively larger cross-sectional opening at or near top surface 14. In such preferred embodiments, support plate 12 is mounted to the vertebrae by way of a number of bone fasteners 40, wherein at least a portion of each bone fastener is tapered to create a cooperative engaging relationship with portions of respective aperture walls e.g. 24, 34 of respective apertures in which the bone fastener is inserted.

Figure 5B:
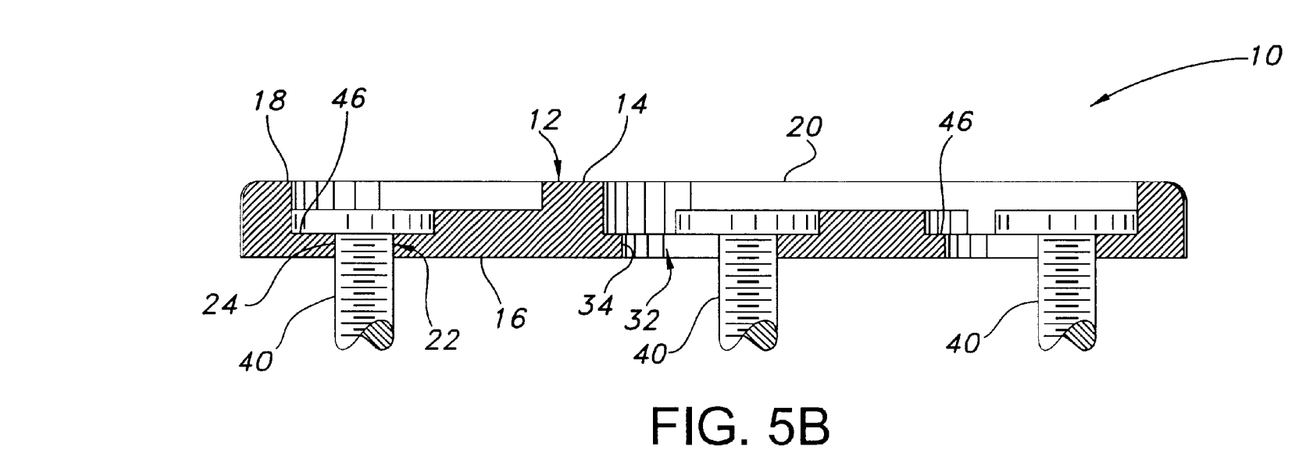

In other embodiments, such as the one illustrated in FIG. 5B, aperture walls 24, 34 comprise bearing surfaces 46 which interface in a cooperative engaging relationship with fasteners 40, such as e.g. headed screws, to limit the fasteners from passing entirely and completely through support plate 12.

Other methods of cooperative engagement between respective bone fasteners 40 and support plate 12 whereby such cooperative engagement secures the support plate to desired bone material, and at the same time, limits the fasteners from passing entirely and completely through support plate 12 will be obvious to those of ordinary skill in art.

Figure 2:
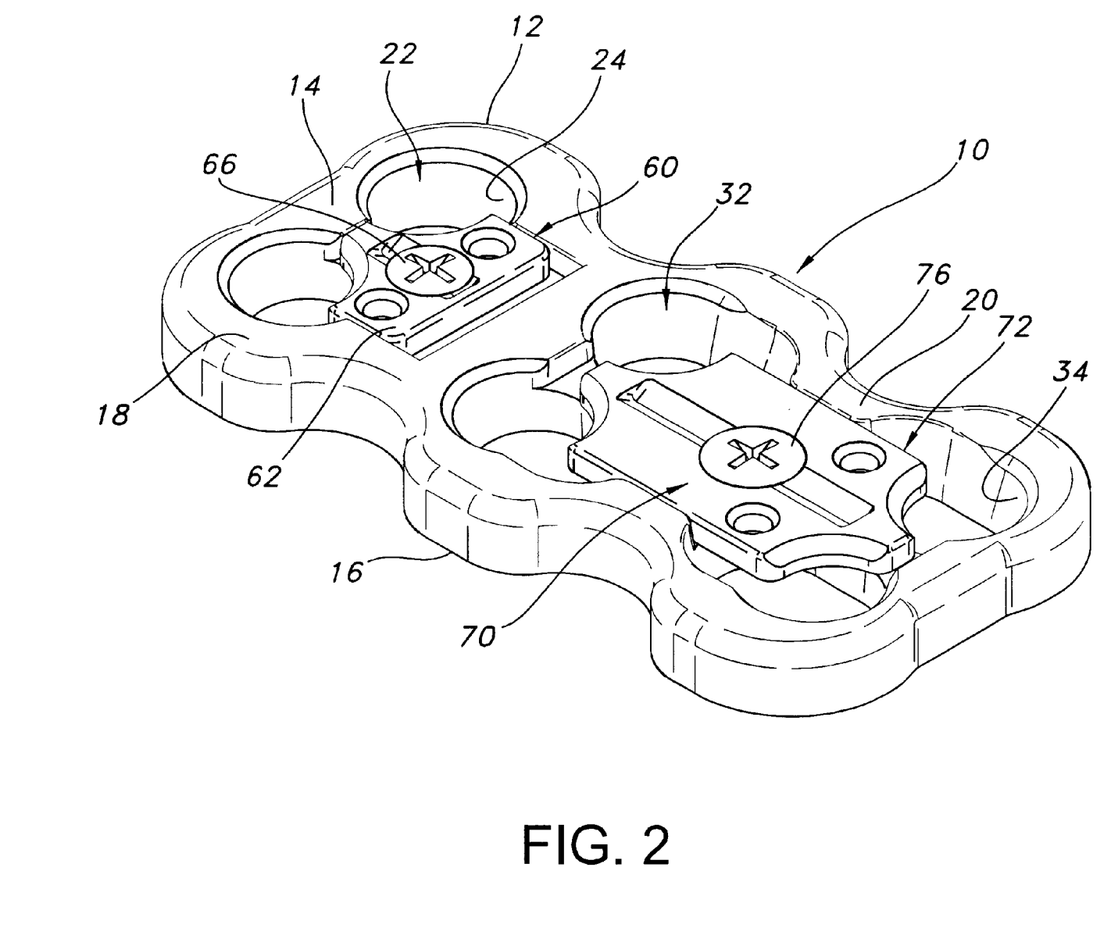
FIG. 2 is an orthogonal view of a bone support assembly of the invention shown with base cover plate and settle cover plate attached.
Figure 3:
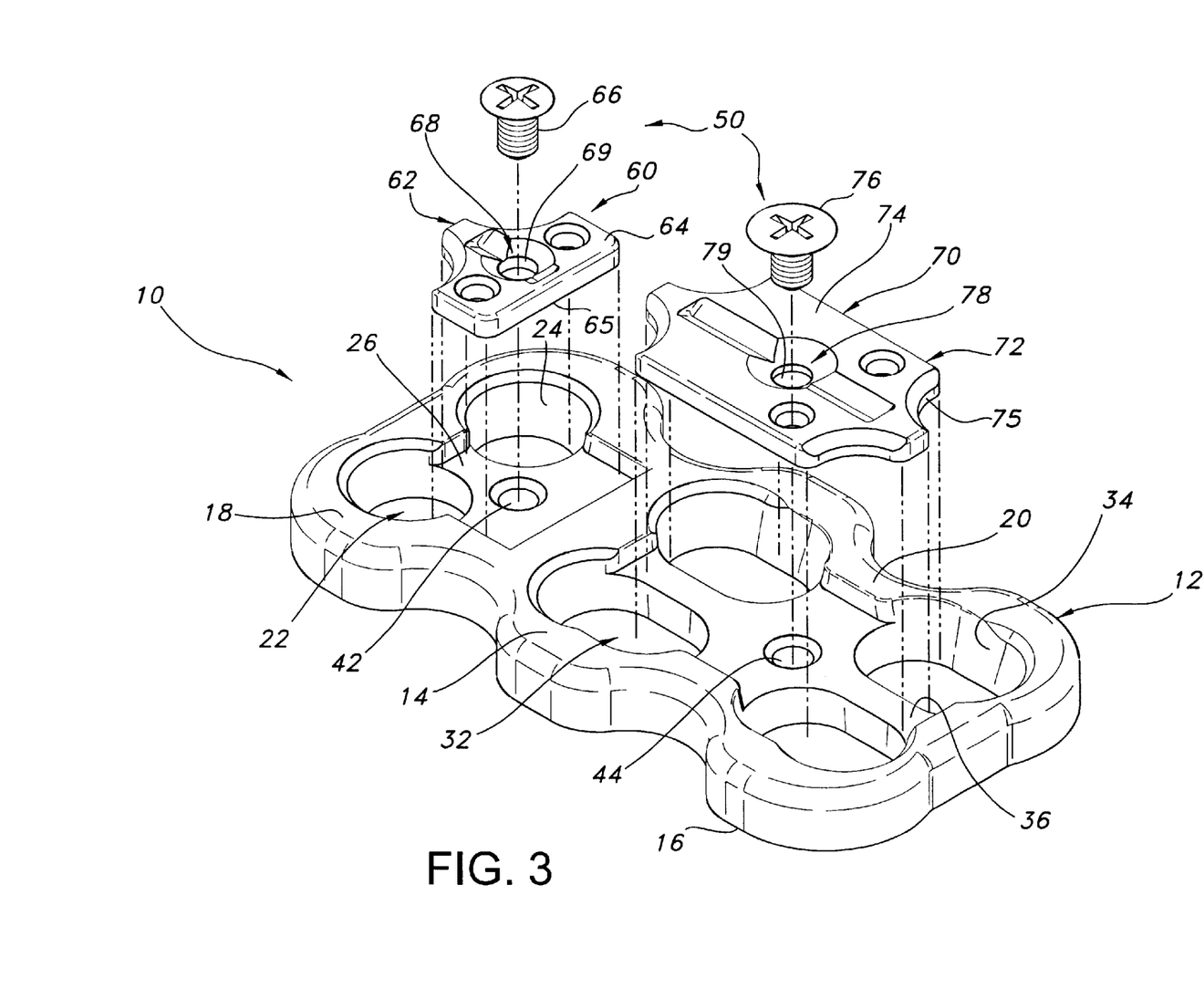
FIG. 3 shows an exploded view of the bone support assembly of FIG. 2, with base cover plate and settle cover plate.
Figure 4:
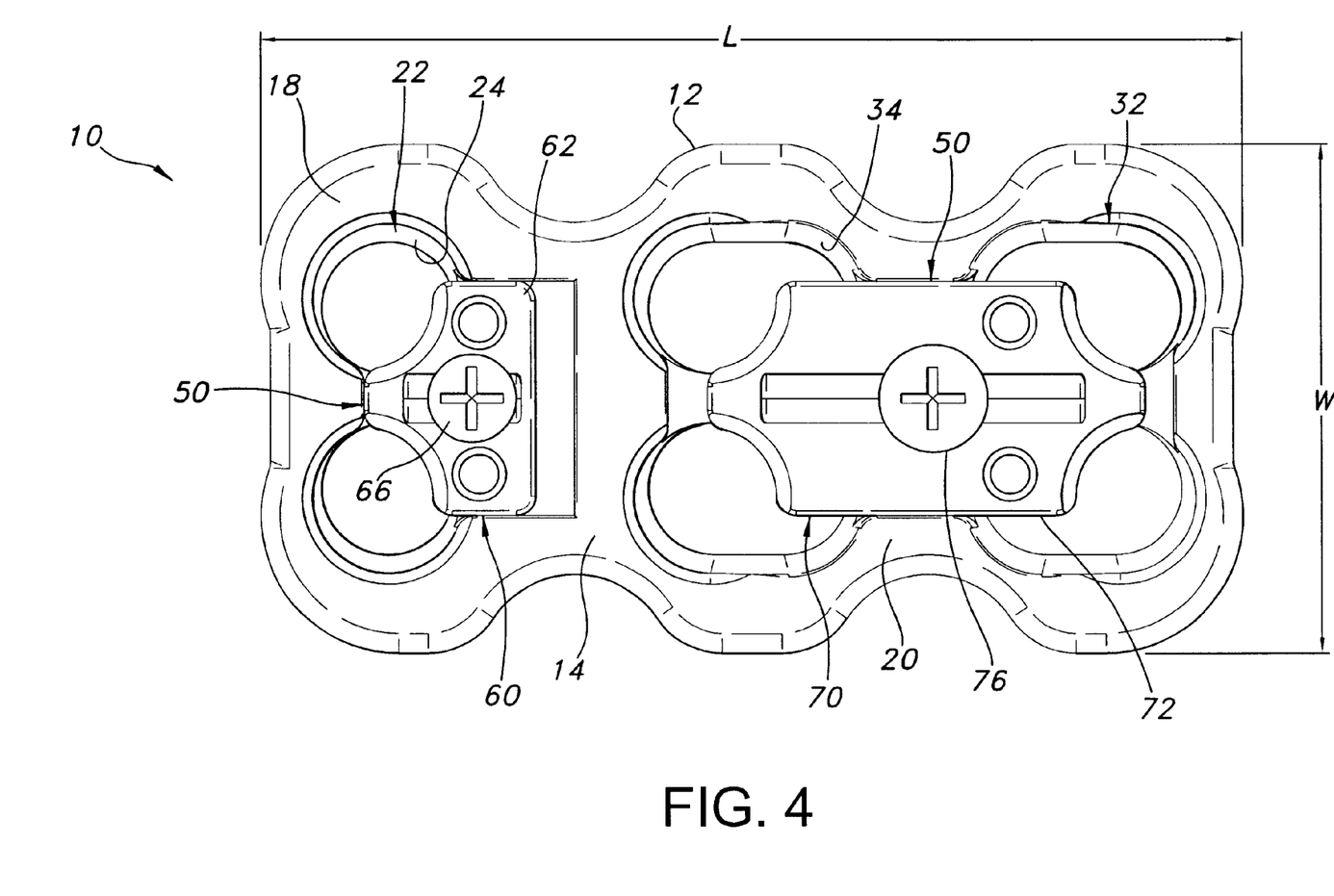
FIG. 4 shows a top view of the bone support assembly illustrated in FIG. 2, and illustrates the over-lapping arrangement of the base cover plate and settle cover plate in relationship to respective apertures of the support plate of the assembly.

Referring to FIG. 1, in preferred embodiments, fixed base portion 18 comprises a base cover plate recess 26, which is disposed adjacent base apertures 22, and configured to accommodate a complimentary base cover plate 62 (FIGS. 2–4). Similarly, slot portion 20 preferably comprises a settle cover plate recess 36, which is disposed adjacent slot-shaped apertures 32, and configured to accommodate a complimentary settle cover plate 72 (FIGS. 2–4). The respective complementary configurations of recesses 26, 36 bidirectionally restrict movement of respective complimentarily configured plates 62, 72, respectively, when such plates are firmly affixed to support plate 12 by fasteners urging plates 62, 72 into respective recesses 26, 36 and toward bottom surface 16 of support plate 12 as in FIGS. 2 and 4.

As previously described, the bone fasteners utilized for securing support plate 12 to underlying bone are generally bone screws of a type well known in the art. Preferably, the bone fasteners utilized in the present invention are of a tapered or modified conical type, reflecting a complementary shape to a respective receiving aperture e.g. 22, 32 of FIG. 5A.

In some embodiments, the bone fastener comprises a screw having a shaft wherein at least a portion of the shaft is generally threaded, and the shaft comprises a head and a tip. The threaded portion of the shaft is threaded to specifically engage bone. The head of the screw is designed and configured to engage a complimentary bearing surface, e.g. 46 of FIG. 5B, which interfaces with the head of the screw to limit the screw from passing entirely and completely through the support plate.

In an alternative mechanism for fixation of support plate assembly 10 to bone material, a headless bone fastener can first be driven into and affixed within the bone material. Support plate 12 of bone support assembly 10 is then disposed over the portion of the bone fastener protruding from the bone material, and the bone fastener is fixed to support plate 12 by threadingly engaging a nut to a nut-receiving portion of the bone fastener with the threads of the nut-receiving portion of the bone fastener protruding from the bone. In such embodiments, the nut, having locking threads, is tightened about the nut-receiving portion of the bone fastener until such nut comes into surface-to-surface contact with a complimentary bearing surface of the support plate, thereby interfacing with the nut to limit the nut-receiving portion, having the nut attached thereto, from passing entirely and completely through the support plate.

It is well understood that bones grow along lines of stress. Therefore, in order for fusion to occur between two or more vertebrae, a graft disposed between the vertebrae must be subjected to compressional forces or stressed for solid bone fusion to occur. Bone fusion tends to be a very dynamic physiological process. Graft material slowly resorbs as osteoclasts remove damaged bone tissue, and osteoblasts replace damaged bone tissue with new living bone tissue. In conventional plate constructs, wherein fasteners hold the vertebral bodies at a fixed apart distance, any resorption of the bone graft reduces or eliminates compressional and/or stress forces on the graft. Accordingly, these conventional plates can induce or cause a condition known as psuedoarthrosis manifesting symptoms of significant pain and swelling in the vertebral area of attachment. Therefore, it is important to maintain the graft under some axial loading forces or stress while allowing the plate to compensate for the bone dynamics. This can be accomplished utilizing the bone support assembly of the invention as described herein.

Referring to FIGS. 1–5B, the spacing and/or orientation of base apertures 22, slot-shaped apertures 32, and fasteners 40 within bone support assembly 10 can be designed and selected so as to achieve a desired dynamic stress-sharing arrangement between the bone fasteners disposed in the various combinations of base apertures 22 and slot-shaped apertures 32 described above. That is, the bone support assembly 10 can be tailored to a specific application such that the stress-load carried by each respective bone fastener can be distributed in a desired manner, including load shifting after support plate 12 of bone support assembly 10 has been affixed to the underlying bone. Thus, bone support assembly 10 can accommodate the dynamic environment into which it is utilized without incurring the drawbacks of the prior art devices described above.

Apertures 32 are slot-shaped in an oblong fashion to accommodate settling of vertebrae as a result of e.g. axial loading after surgical attachment to the vertebrae. The apertures can allow for vertebral settling of about 5–6 millimeters, and preferably about 2–3 millimeters. Sizes of apertures 32 are not contemplated as being limited to a range of 5–6 millimeters, but are contemplated as being designed and configured to reflect a size great enough to enable sufficient vertebral settling as a result of e.g. axial loading.

In all of the embodiments shown in FIGS. 1–5B, elongate slot-shaped apertures 32 are capable of receiving at least one bone fastener therein. The bone fasteners can be affixed within slot-shaped apertures 32 in a manner similar to that discussed above. Elongate slot-shaped apertures 32 enable a substantial margin for adjustment and proper location of the bone fastener with relationship to the support plate and, as discussed above, the bone fasteners can be made to slide freely with relationship to aperture walls 34 of slot-shaped apertures 32.

Support plate 12 can comprise a bone engagement surface disposed on bottom surface 16 of support plate 12 for enhancing the engagement of support plate 12 to the vertebrae. Preferably, the bone engagement surface includes a texturized surface disposed on substantially all of bottom surface 16 of the support plate 12. In other embodiments, the texturized surface can be disposed on only a portion of bottom surface 16. The texturized surface of bottom surface 16 of support plate 12 can include etched, roughened, grooved, knurled, or other substantially functional contouring equivalent as is known to those skilled in the art.

In some embodiments, a bone fastener cover assembly 50 comprises at least one cover plate, wherein the bone fastener cover assembly is designed and configured to overlap at least portions of ones of the apertures thus preventing a "backing out" of bone fasteners from the bone to which the bone fasteners are implanted. In the embodiments illustrated in FIGS. 2–4, bone fastener cover assembly 50 is illustrated in two portions comprising a base portion cover assembly 60 and a slot-portion cover assembly 70. Cover assemblies 60, 70 preferably are designed and configured to engage in a complementary relationship with respective recesses 26, 36, respectively, disposed on support plate 12. The illustrated embodiments reflect base cover plate recess 26, and settle cover plate recess 36, being adapted to receive complimentary base cover plate 62 and settle cover plate 72, respectively. The location and configuration of the recesses can be varied according to a desired or specific cover plate(s) to be utilized for the purpose of preventing backing out of the fasteners in a variety of different sized apertures.

Referring to the embodiments illustrated in FIGS. 2–4, bone support assembly 10 comprises base portion cover assembly 60 comprising base cover plate 62 having an upper surface 64 and a lower surface 65, at least one base cover plate fastener 66, and at least one base cover plate aperture 68, ones of the base cover plate apertures 68 having aperture walls 69. Similarly, bone support assembly 10 also comprises slot portion cover assembly 70 comprising settle cover plate 72 having a superior surface 74 and an inferior surface 75, at least one settle cover plate fastener 76, and at least one settle cover plate aperture 78, ones of the settle cover plate apertures 78 having aperture walls 79.

Base cover plate 62 of base portion cover assembly 60 is affixed to support plate 12 via inserting base cover plate fastener 66 through base cover plate aperture 68 and engaging base cover plate fastener 66 with a first base plate fastener aperture 42 disposed in support plate 12, wherein first base plate fastener aperture 42 reflects an engagement relationship with base cover plate fastener 66. Similarly, settle cover plate 72 of slot portion cover assembly 70 is affixed to support plate 12 via inserting settle cover plate fastener 76 through settle cover plate aperture 78 and engaging settle cover plate fastener 76 with a second settle plate fastener aperture 44 disposed in support plate 12, wherein second settle plate fastener aperture 44 reflects an engagement relationship with settle cover plate fastener 76.

In preferred methods of affixing bone support assembly 10 to bone material, the method comprises bidirectionally adjusting one or both settle cover plate 72 and base cover plate 62 about settle cover plate fastener 76 and base cover plate fastener 66, respectively, to enable a surgeon, or other inserter, during the surgical procedure, to insert the bone fasteners into respective apertures, thus providing a support backing for the bone support assembly while maintaining a connection of backing plates 62, 72, thus reducing the potential number of loose components of the bone support assembly.

Referring to FIG. 3, the size of base cover plate aperture 68 is preferably greater than the size of the shaft of corresponding base cover plate fastener 66 by a first dimension greater than or substantially equal to that amount of bidirectional movement of base cover plate 62 about base cover plate fastener 66, relative to support plate 12 necessary to gain fastening access to at least one bone fastener while prohibiting fastening access to at least another bone fastener, wherein each of the first bone fasteners is disposed in a separate and distinct base aperture 22, and whereby at no time are all bone fasteners accessible for fastening to the bone structure.

Still referring to FIG. 3, base apertures 22 are preferably not designed to provide for longitudinal movement of bone fasteners 40 in apertures 22. Thus, the size of the respective portions of apertures 22 which are substantially aligned with the top surface of base cover plate recess 26 preferably is substantially equal to the size of the portion of the bone fastener most remote from the supported bone. The amount of overlap of base cover plate 62 over bone fasteners in each of apertures 22, when base cover plate 62 is firmly affixed in a tightened position to support plate 12, as in FIGS. 2 and 4, directly affects the required difference in respective cross-sectional sizes between the shaft of base cover plate fastener 66 and the narrowest portion of base cover plate aperture 68. So if base cover plate 62, in such plate's tightened position, as in FIGS. 2 and 4, overlaps bone fasteners in each of apertures 22 by e.g. approximately 0.5 mm, the respective cross-sectional size of the narrowest portion of base cover plate aperture 68 must be at least e.g. about 1.0 mm greater than the cross-sectional size of the shaft of base cover plate fastener 66, thus allowing for one or both longitudinal and transverse movement of at least e.g. about 0.5 mm of plate 66 about the shaft of fastener 66 when such fastener is not fully engaged into aperture 68, thereby enabling bidirectional adjustment of plate 62.

Regardless of the chosen embodiment, the cross-sectional size of the narrowest portion of base cover plate aperture 68 is preferably equal to or greater than the sum of the cross-sectional size of the shaft of base cover plate fastener 62 plus two times the amount of overlap of base cover plate 62 over bone fasteners in each of apertures 22. Thus, if base cover plate 62 overlaps bone fasteners in each of apertures 22 by 0.75 mm, and the cross-sectional size of the shaft of base cover plate fastener 66 is 2.0 mm, the cross-sectional size of the narrowest portion of base cover plate aperture 68 is no less than 3.5 mm.

Again referring to FIG. 3, while the shaft of base cover plate fastener 66 has a smaller cross-sectional size than that of base cover plate aperture 68, the shape and cross-sectional area of fastener 66 is complimentary to the shape and cross-sectional area of base plate fastener aperture 42, thus enabling cooperative fastening engagement between fastener 66 and the walls of base plate fastener aperture 42. Thus, when base cover plate fastener 66 is generally inserted through base cover plate aperture 68 and only partially engaged into base plate fastener aperture, base cover plate 62 can be bidirectionally adjusted to access bone fasteners 40 disposed in either of apertures 22 while still maintaining connection to support plate 12.

The head of base cover plate fastener 66 and a portion of wall 69 of base cover plate aperture 68 have complimentary tapered configurations wherein the cross-sectional opening of aperture 68 adjacent the upper surface of plate 62 is greater than the cross-sectional opening of aperture 68 adjacent the lower surface of plate 62. Such a complimentary tapered configuration enables a installer to fully impede bidirectional movement of base cover plate 62 about base cover plate fastener 66 by tightening fastener 66 into a fully engaged relationship with bone plate fastener aperture 42.

Similarly, the size of settle cover plate aperture 78 is preferably greater than the size of the shaft of settle cover plate fastener 76 by a first measure greater than or substantially equal to that amount of bidirectional movement of settle cover plate 72 about settle cover plate fastener 76, relative to support plate 12 necessary to gain fastening access to at least one bone fastener while prohibiting fastening access to at least another bone fastener, wherein each of the first bone fasteners is disposed in a separate and distinct slot-shaped aperture 32, and whereby at no time are all bone fasteners accessible for fastening to the bone structure.

Still referring to FIG. 3, slot-shaped apertures 32 are preferably designed to provide for longitudinal movement of bone fasteners 40 in apertures 32, thus allowing settling of supported vertebrae. Therefore, the largest transverse distance of the respective portions of apertures 32, which are substantially aligned with the top surface of settle cover plate recess 36, is substantially equal to the size of the portion of the bone fastener most remote from the supported bone. The amount of overlap of settle cover plate 72 over bone fasteners in each of apertures 32, when settle cover plate 72 is firmly affixed in a tightened position to support plate 12, as in FIGS. 2 and 4, directly affects the required difference in cross-sectional sizes between the shaft of settle cover plate fastener 76 and the narrowest portion of settle cover plate aperture 78. So if settle cover plate 72, in such plate's tightened position, overlaps bone fasteners in each of apertures 32 by e.g. approximately 0.6 mm, the cross-sectional size of the narrowest portion of settle cover plate aperture 78 must be at least e.g. about 1.2 mm greater than the cross-sectional diameter of the shaft of settle cover plate fastener 76, thus allowing for one or both longitudinal and transverse movement of at least e.g. about 0.6 mm of plate 76 about the shaft of fastener 76 when such fastener is not fully engaged into aperture 78, thereby enabling bidirectional adjustment of plate 72.

Generally, the cross-sectional size of the narrowest portion of settle cover plate aperture 78 is preferably equal to or greater than the sum of the cross-sectional size of the shaft of settle cover plate fastener 72 and two times the amount of overlap of settle cover plate 72 over bone fasteners in each of apertures 32. Thus, if settle cover plate 72 overlaps bone fasteners in each of apertures 32 by 0.8 mm, and the cross-sectional size of the shaft of settle cover plate fastener 76 is 2.2 mm, the cross-sectional size of the narrowest portion of settle cover plate aperture 78 is no less than 3.8 mm.

Still referring to FIG. 3, while the shaft of settle cover plate fastener 76 has a smaller cross-sectional size than that of settle cover plate aperture 78, the shape and cross-sectional area of fastener 76 is complimentary to the shape and cross-sectional area of settle plate fastener aperture 44 thus enabling cooperative fastening engagement between fastener 76 and the walls of settle plate fastener aperture 44. Thus, when settle cover plate fastener 76 is generally inserted through settle cover plate aperture 78 and only partially engaged into settle plate fastener aperture, settle cover plate 72 can be bidirectionally adjusted to access bone fasteners 40 disposed in either of apertures 32 while still maintaining connection to support plate 12.

As with the base cover plate fastener, the head of settle cover plate fastener 76 and a portion of wall 79 of settle cover plate aperture 78 have complimentary tapered configurations wherein the cross-sectional opening of aperture 78 adjacent the upper surface of plate 72 is greater than the cross-sectional opening of aperture 78 adjacent the lower surface of plate 72. Such a complimentary tapered configuration enables a installer to fully impede bidirectional movement of settle cover plate 72 about settle cover plate fastener 76 by tightening fastener 76 into a fully engaged relationship with bone plate fastener aperture 44.

The above-described embodiments generally reflect laterally-symmetric embodiments of support plate 12 having pairs of either circular or elongate, slot-shaped apertures, wherein a first aperture of each pair is located on a first side of longitudinal axis 28, and a second aperture of each pair is located on a second side of longitudinal axis 28, as in FIG. 1. While laterally-symmetric embodiments are preferred, other embodiments of the invention are contemplated, such as embodiments wherein respective apertures, e.g. 22, 32, have cross-sectional shapes other than circular or elongate. In other embodiments, apertures, e.g. 22, 32, are not aligned, but are arranged in a staggered configuration. In yet other embodiments, a cover plate may cover a first respective bone fastener in an aperture more or less than such cover plate covers a second respective bone fastener, such that the respective cover plate aperture, e.g. 68, 78, is not substantially circular, but e.g. elongate and/or slot-shaped, to accommodate sufficient bidirectional movement to access respective bone fasteners in respective apertures. Other embodiments of the invention will be obvious to those of ordinary skill in the art.

Bone support assembly 10 is preferably affixed to the anterior portion of desired vertebrae of the recipient such that fixed base portion 18 is disposed and attached to the most caudal of the desired vertebrae. Accordingly, slot portion 20 is preferably disposed and attached to the more cephalic of the desired vertebrae, wherein the most caudal of the desired vertebrae assists in providing a foundation or base contributing to supporting ones of the more cephalic vertebrae.

Bone support assembly 10 can be constructed of any suitable material. Preferably, bone support assembly 10 and other components, such as the fasteners, are constructed of suitable materials which are compatible with the uses and environments into which bone support assembly 10 will be utilized. Preferably, bone support assembly 10 is constructed of metallic materials such as titanium, stainless steel, or other metal alloys. The material which bone support assembly 10 is constructed of should have strength and be non-reactive and non-antigenic to biological systems.

Those skilled in the art will now see that certain modifications can be made to the apparatus and methods herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

To the extent the following claims use means plus function language, it is not meant to include there, or in the instant specification, anything not structurally equivalent to what is shown in the embodiments disclosed in the specification.

Having thus described the invention, what is claimed is:

1. A bone support plate for use in a bone support assembly, said bone support plate comprising:

(a) a top surface;

(b) a bottom surface opposite the top surface and adapted to engage bone structure of a user;

(c) a fixed base portion, having first and second apertures extending therethrough, from the top surface to the bottom surface, for receiving bone fasteners therethrough;

(d) a first base cover plate recess in the top surface at said fixed base portion for receiving a base cover plate thereonto and accommodating sliding movement of such base cover plate to impose and withdraw at least partial obstruction of the first and second apertures;

(e) a slot portion, having at least third and fourth apertures extending therethrough, from the top surface to the bottom surface, for receiving bone fasteners therethrough, said apertures in said bone support plate being shaped to accommodate settling of vertebrae after surgical attachment of said bone support plate to such vertebrae; and (f) a second settle cover plate recess in the top surface at said slot portion for receiving a settle cover plate thereonto and accommodating sliding movement of such settle cover plate to impose and withdraw at least partial obstruction of the third and fourth apertures.

2. A bone support plate as in claim 1, said at least third and fourth apertures of said slot portion being longitudinally slot-shaped, with respect to a longitudinal axis of said support plate, to enable respective bone fasteners to be inserted into respective said at least third and fourth apertures such that the slot-shaped apertures accommodate movement of the bone support plate with respect to such bone fasteners.

3. A bone support plate as in claim 1, said third and fourth apertures being sized and configured to accommodate vertebral settling of at least about 2 millimeters.

4. A bone support plate as in claim 1, said third and fourth apertures being sized and configured to accommodate vertebral settling of about 5–6 millimeters.

5. A bone support plate as in claim 1, said third and fourth apertures being sized and configured to enable sufficient vertebral settling as a result of axial loading.

6. A bone support assembly for support of bone structure, said bone support assembly comprising:

(a) a support plate comprising a top surface, a bottom surface adapted to engage such bone structure, a fixed base portion, and a slot portion, said fixed base portion comprising base apertures, said slot portion comprising slot-shaped apertures;

(b) bone fasteners disposed in ones of the base apertures and the slot-shaped apertures, said bone fasteners and said support plate, in combination, being adapted and configured for holding said support plate to bone material; and (c) a bone fastener cover assembly, said bone fastener cover assembly comprising a cover plate, and at least one cover plate fastener effective to fasten said cover plate to said support plate, said at least one cover plate and said support plate, in combination, accommodating both longitudinal and transverse sliding movement of said cover plate with respect to said support plate, to thereby cover and uncover ones of said bone fasteners while said cover plate is attached to said support plate, including uncovering one of a pair of bone fasteners arranged in side-by-side relationship along the longitudinal axis of said support plate, while relatively covering the other of such pair of bone fasteners.

7. A bone support assembly as in claim 6 wherein said cover plate of said bone fastener cover assembly simultaneously covers, at least in part, said bone fasteners in at least 4 slot-shaped apertures of said support plate, where one or both longitudinal and transverse movement of said cover plate tends to simultaneously cover a said bone fastener in at least one aperture while uncovering another said bone fastener in another aperture, whereby at no time are said bone fasteners in all apertures uncovered.

8. A bone support assembly for support of bone structure, said bone support assembly comprising:

(a) a support plate comprising a top surface, a bottom surface adapted to engage such bone structure, a fixed base portion, and a slot portion, said fixed base portion comprising base apertures, said slot portion comprising slot-shaped apertures;

(b) bone fasteners disposed in ones of the base apertures and the slot-shaped apertures, said bone fasteners and said support plate, in combination, being adapted and configured for holding said support plate to bone material, said slot-shaped apertures being adapted to accommodate settling of vertebrae after surgical attachment of said bone support plate to such vertebrae;

(c) a base portion cover assembly disposed at said fixed base portion; and (d) as a separate and distinct element, a slot portion cover assembly disposed at said slot portion.

9. A bone support assembly as in claim 8, said base portion cover assembly comprising a base cover plate having an upper surface and a lower surface, at least one base cover plate fastener, and at least one base cover plate aperture spanning from the upper surface of said base cover plate toward the lower surface of said base cover plate.

10. A bone support assembly as in claim 9, said at least one base cover plate aperture comprising an aperture wall, wherein an upper portion of said aperture wall comprises an inwardly-tapered frustoconical configuration extending inwardly toward the lower surface of said base cover plate.

11. A bone support assembly as in claim 9, said slot portion cover assembly comprising a settle cover plate having a superior surface and an inferior surface, at least one settle cover plate aperture spanning from said superior surface to said inferior surface of said settle cover plate, and at least one settle cover plate fastener in said at least one settle cover plate aperture.

12. A bone support assembly as in claim 8 wherein said base cover plate and said support plate, in combination, are designed and configured to enable both longitudinal and transverse adjustment of said base cover plate, with respect to said support plate, while maintaining said support plate connected to said base cover plate.

13. A bone support assembly as in claim 8, said at least one settle cover plate aperture comprising an aperture wall, wherein an upper portion of said aperture wall comprises an inwardly-tapered frustoconical configuration adjacent the superior surface of said settle cover plate and extending toward the inferior surface of said settle cover plate.

14. A bone support assembly as in claim 8, said slot portion cover assembly comprising a settle cover plate, said settle cover plate overlapping a portion of at least one said bone fastener in at least one said slot-shaped aperture of said support plate.

15. A bone support assembly as in claim 14 wherein said settle cover plate and said support plate are, in combination, designed and configured to enable both longitudinal and transverse adjustment of said settle cover plate, with respect to said support plate, while maintaining said support plate connected to said settle cover plate.

16. A bone support assembly as in claim 15 wherein said settle cover plate can simultaneously cover, at least in part, said bone fasteners in at least 4 slot-shaped apertures of said slot portion, where one or both longitudinal and transverse movement of said settle cover plate tends to simultaneously cover a said bone fastener in at least one said aperture while uncovering another said bone fastener in another said aperture, whereby at no time are all bone fasteners in all apertures uncovered.

17. A bone support assembly as in claim 8 wherein the slot-shaped apertures are designed and configured to enable respective bone fasteners to be inserted into respective said slot-shaped apertures such that the slot-shaped apertures accommodate movement of the bone support plate with respect to the bone fasteners.

18. A bone support plate as in claim 8, said slot-shaped apertures being sized and configured to accommodate vertebral settling of at least about 2 millimeters.

19. A bone support plate as in claim 8, said slot-shaped apertures being sized and configured to accommodate vertebral settling of about 5–6 millimeters.

20. A bone support plate as in claim 8, said slot-shaped apertures being sized and configured to enable sufficient vertebral settling as a result of axial loading.

21. A bone support assembly for support of bone structure, said bone support assembly comprising:
  (a) a support plate comprising a top surface, a bottom surface adapted to engage such bone structure, a fixed base portion, and a slot portion, said fixed base portion comprising base apertures, said slot portion comprising slot-shaped apertures;
  (b) bone fasteners disposed in ones of the base apertures and the slot-shaped apertures, said bone fasteners and said support plate, in combination, being adapted and configured for holding said support plate to bone material;
  (c) a base portion cover assembly disposed at said fixed base portion; and
  (d) a slot portion cover assembly disposed at said slot portion,
said base portion cover assembly comprising a base cover plate having an upper surface and a lower surface, at least one base cover plate fastener, and at least one base cover plate aperture spanning from the upper surface of said base cover plate toward the lower surface of said base cover plate, size of said at least one base cover plate aperture being greater than a corresponding size of said at least one base cover plate fastener by a first dimension greater than or substantially equal to that amount of bidirectional movement of said base cover plate about said base cover plate fastener relative to said support plate necessary to gain fastening access to at least one said bone fastener of said support plate while prohibiting fastening access to at least another said bone fastener, whereby at no time are all bone fasteners accessible for fastening to said bone structure.

22. A bone support plate as in claim 21, said slot-shaped apertures being sized and configured to accommodate vertebral settling of at least about 2 millimeters.

23. A bone support assembly for support of bone structure, said bone support assembly comprising:
  (a) a support plate comprising a top surface, a bottom surface adapted to engage such bone structure, a fixed base portion, and a slot portion, said fixed base portion comprising base apertures, said slot portion comprising slot-shaped apertures;
  (b) bone fasteners disposed in ones of the base apertures and the slot-shaped apertures, said bone fasteners and said support plate, in combination, being adapted and configured for holding said support plate to bone material;
  (c) a base portion cover assembly disposed at said fixed base portion; and
  (d) a slot portion cover assembly disposed at said slot portion, said base portion cover assembly comprising a base cover plate, said base cover plate overlapping a portion of at least one said bone fastener in at least one of said base apertures of said support plate, said bone support assembly including a slot in at least one of said base cover plate and said support plate, accommodating sliding of said base cover plate into overlying relationship with first ones of said bone fasteners, and out of overlying relationship with second ones of said bone fasteners.

24. A bone support plate as in claim 23, said slot-shaped apertures being sized and configured to accommodate vertebral settling of at least about 2 millimeters.

25. A bone support assembly for support of bone structure, said bone support assembly comprising:
  (a) a support plate comprising a top surface, a bottom surface adapted to engage such bone structure, a fixed base portion, and a slot portion, said fixed base portion comprising base apertures, said slot portion comprising slot-shaped apertures;
  (b) bone fasteners disposed in ones of the base apertures and the slot-shaped apertures, said bone fasteners and said support plate, in combination, being adapted and configured for holding said support plate to bone material;
  (c) a base portion cover assembly disposed at said fixed base portion; and
  (d) a slot portion cover assembly disposed at said slot portion, said slot portion cover assembly comprising a settle cover plate, said settle cover plate overlapping a portion of at least one said bone fastener in at least one said slot-shaped aperture of said support plate,
wherein said settle cover plate can simultaneously cover, at least in part, said bone fasteners in at least 4 slot-shaped apertures of said slot portion, where one or both longitudinal and transverse movement of said settle cover plate tends to simultaneously cover a said bone fastener in at least one said aperture while uncovering another said bone fastener in another said aperture, whereby at no time are all bone fasteners in all apertures uncovered.

26. A bone support plate as in claim 25, said slot-shaped apertures being sized and configured to accommodate vertebral settling of at least about 2 millimeters.

27. A method of mounting a support to bone structure, the method comprising:
  (a) providing a bone support assembly comprising
    (i) a support plate adapted to support bone structure, the support plate comprising a fixed base portion having base apertures, and a slot portion having slot-shaped apertures,
    (ii) bone fasteners in ones of the base apertures and the slot-shaped apertures, and
    (iii) a cover plate disposed over a top surface of the support plate;
  (b) moving the bone support assembly into position over bone structure to be supported;
  (c) sliding the cover plate, as necessary, away from a position over ones but not all of the bone fasteners thus to expose such fasteners for fastening while prohibiting fastening access to at least another of the bone fasteners, and fastening the so- exposed bone fasteners to the bone structure; and (d) sliding the cover plate at least partially over the bone fasteners so fastened and tightening the cover plate to the support plate thereby to prevent movement of the cover plate with respect to the fastened bone fasteners and correspondingly preventing extraction of the fastened bone fasteners from the bone structure.

28. A method of mounting a support to bone structure as in claim 27, the cover plate being disposed over the base apertures at the fixed base portion, the method further including (e) providing a settle plate over a second portion of the top surface of the support plate at the slot portion;

(f) sliding the settle plate away from the position over additional respective ones of the bone fasteners disposed in the slot-shaped apertures, and fastening the respective bone fasteners, in the slot-shaped apertures, to the bone structure; and (f) sliding the settle plate at least partially over the respective fastened bone fasteners and tightening the settle plate to the support plate thereby to prevent movement of the settle plate, and correspondingly preventing extraction of the fastened bone fasteners.

29. A bone support plate as in claim 27, said slot-shaped apertures being sized and configured to accommodate vertebral settling of at least about 2 millimeters.

30. A bone support plate as in claim 27, said slot-shaped apertures being sized and configured to accommodate vertebral settling of about 5–6 millimeters.

31. A bone support plate as in claim 27, said slot-shaped apertures being sized and configured to enable sufficient vertebral settling as a result of axial loading.

32. A method of mounting a support to bone structure, the method comprising:

(a) providing a bone support assembly comprising
  (i) a support plate adapted to support bone structure, the support plate comprising a fixed base portion having base apertures, and a slot portion having slot-shaped apertures,
  (ii) bone fasteners in ones of the base apertures and the slot-shaped apertures, and
  (iii) a cover plate disposed over a top surface of the support plate, the cover plate being disposed over the base apertures at the fixed base portion;

(b) moving the bone support assembly into position over bone structure to be supported;

(c) sliding the cover plate, as necessary, away from a position over ones but not all of the bone fasteners thus to expose such fasteners for fastening, and fastening the bone fasteners to the bone structure; and (d) sliding the cover plate at least partially over the bone fasteners so fastened and tightening the cover plate to the support plate thereby to prevent movement of the cover plate with respect to the fastened bone fasteners and correspondingly preventing extraction of the fastened bone fasteners from the bone structure;

(e) providing a settle plate over a second portion of the top surface of the support plate at the slot portion;

(f) sliding the settle plate away from the position over additional respective ones of the bone fasteners disposed in the slot-shaped apertures, and fastening the respective bone fasteners, in the slot-shaped apertures, to the bone structure; and (g) sliding the settle plate at least partially over the respective fastened bone fasteners and tightening the settle plate to the support plate thereby to prevent movement of the settle plate, and correspondingly preventing extraction of the fastened bone fasteners, the method including using the settle plate to simultaneously cover, at least in part, the bone fasteners in each of at least 4 slot-shaped apertures of the slot portion, where one or both longitudinal and transverse movement of the settle plate tends to simultaneously cover a respective bone fastener in at least one aperture while uncovering another respective bone fastener in another aperture, whereby at no time are all bone fasteners in all apertures uncovered.

33. A method of distributing stress loads carried by bone fasteners used to attach a spinal support plate to first and second vertebrae of a spinal column, the method comprising attaching a bone support plate to vertebrae in the spinal column by a combination of (i) first bone fasteners extending through base apertures (22) which are not designed to provide for longitudinal movement of the bone fasteners, and (ii) second bone fasteners extending through slot-shaped apertures (32) which are designed to provide for longitudinal movement of the bone fasteners to accommodate settling of the vertebrae, the combination of the base apertures (22) and the slot-shaped apertures (32), with the respective first and second bone fasteners therein, allowing post-procedural compression between the respective vertebrae, which enables maintaining the first and second vertebrae under post-procedural axial loading.

34. A method as in claim 33 wherein the apertures (32) are sized and configured to accommodate vertebral settling of at least about 2 millimeters.

35. A method as in claim 33 wherein the apertures (32) are sized and configured to accommodate vertebral settling of about 5–6 millimeters.

36. A method as in claim 33 wherein the apertures (32) are sized and configured to enable sufficient vertebral settling as a result of axial loading.

37. A bone support plate comprising a top surface, a bottom surface, a length, and a width, first base apertures (22) which are not designed to provide for longitudinal movement of first bone fasteners, and second apertures (32) which are designed to provide for longitudinal movement of second bone fasteners to accommodate settling of vertebrae when said bone support plate is attached to such vertebrae, the combination of the first (22) and second (32) apertures, with respective such first and second bone fasteners therein, allowing post-procedural compression of the respective said vertebrae, which enables maintaining the first and second vertebrae under post-procedural axial loading.

38. A bone support plate as in claim 37 wherein the apertures (32) are sized and configured to accommodate vertebral settling of at least about 2 millimeters.

39. A bone support plate as in claim 37 wherein the apertures (32) are sized and configured to accommodate vertebral settling of about 5–6 millimeters.

40. A bone support plate as in claim 37 wherein the apertures (32) are sized and configured to enable sufficient vertebral settling as a result of axial loading.

* * * * *